United States Patent [19]

Bohl et al.

[11] 4,433,922
[45] Feb. 28, 1984

[54] CALORIMETER

[75] Inventors: Thomas L. Bohl, Madison; Pocock, Robert E., Highland Heights; Sharon L. Zimmerlin, Chagrin Falls, all of Ohio

[73] Assignee: The Babcock & Wilcox Company, New Orleans, La.

[21] Appl. No.: 394,955

[22] Filed: Jul. 2, 1982

[51] Int. Cl.³ ............................................. G01N 25/22
[52] U.S. Cl. ...................................... 374/36; 204/424
[58] Field of Search ................ 374/36, 37; 204/195 S, 204/195 P, 1 S, 1 T

[56] References Cited

U.S. PATENT DOCUMENTS 2,689,478  9/1954  Barnard et al. ......................... 374/37
4,329,873  5/1982  Maeda .................................... 374/37
4,359,284 11/1982  Kude et al. ............................ 374/37

FOREIGN PATENT DOCUMENTS 8151  2/1980  European Pat. Off. .............. 374/37

*Primary Examiner*—R. L. Andrews
*Assistant Examiner*—Terryence F. Chapman
*Attorney, Agent, or Firm*—Vytas R. Matas; Robert J. Edwards

[57] ABSTRACT

A calorimeter and method of obtaining the calorific value of a test gas comprises a pair of constant flow pumps one for supplying air at known volumetric flow and the other for supplying a test gas at known volumetric flow. The known volumetric flow of air is maintained at a level sufficient to provide enough oxygen to fully burn all oxidizable components of the test gas. The air and test gas are mixed and catalytically burned in a heated block and the combustion products are thereafter supplied to an electrochemical oxygen measuring cell which measures the remaining oxygen in the mixture. A circuit arrangement is utilized to obtain a value proportional to the difference between the remaining oxygen and original amount of oxygen which value is proportional to the amount of oxygen utilized and in turn proportional to calorific value of the test gas.

5 Claims, 2 Drawing Figures

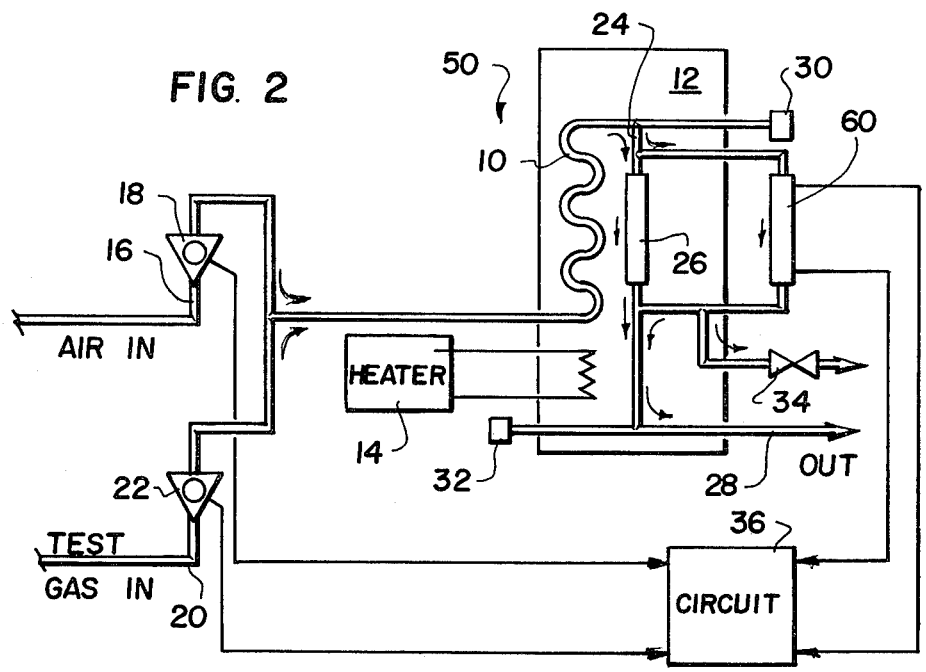

CALORIMETER

FIELD AND BACKGROUND OF THE INVENTION

The present invention relates in general to calorimeters and in particular to a new and useful calorimeter and technique which measures the amount of oxygen utilized in completely catalytically burning combustible products in a test sample, which amount is proportional to the calorific value of the test sample.

Various techniques of calorimetry are known. One such technique known as water-flow calorimetry, relies on the principle of operation wherein heat is transferred by the combustion of a continuous flowing gas to continuously flowing water. The amount of water and the volume of gas combusted are known and the rise of temperature in the water is measured. A disadvantage of this technique is in response time, losses due to heat exchange with surrounding and the difficulty of insuring complete transfer of heat from the combustion products to the water.

Another technique known as differential expansion calorimetry has been utilized by the Sigma Instrument Company Limited and is disclosed in a publication by that company entitled "Mark II Recording Calorimeter for Trouble-Free Recording". In this device the heat capacity of specific gases is obtained by venting the hot combustion products through two concentrically mounted metal tubes. The differential expansion of the tubes has a direct relationship to the thermal input of the gas being burned. The disadvantage of this technique again is heat exchange with the surroundings, particularly where the instrument might be heated unequally.

SUMMARY OF THE INVENTION

The present invention takes advantage of the phenomenon that the amount of oxygen required for combustion is proportional to the calorific value of a gas. See Gas Calorimetry, C. G. Hyde and M. W. Jones, Ernest Benn Limited, London, 1960, page 411. The invention takes advantage of this principle and utilizes an electrochemical measuring cell, specifically $ZrO_2$ fuel cell to measure an amount of oxygen remaining in a known sample of oxygen containing gas after the oxygen containing gas has been used to oxidize a test gas. Details of this fuel cell are not given here but can be discovered for example from U.S. Pat. No. 3,597,345 to Hickam et al.

According to the invention, the calorific value of a test gas can be obtained in a real-time measurement which can be utilized for a control function or simply as an indicator value.

For the complete oxidation of the test or sample gas, a catalytic burning chamber is utilized which is elevated to a high temperature of about 1500° F. This catalytic burning is utilized rather than flame burning since flame burning can seldom achieve complete oxidation due to the masking of unreacted molecules by reaction products.

Accordingly an object of the present invention is to provide a calorimeter for the continuous monitoring of the calorific value of a test gas comprising, first constant flow means for supplying a constant known volumetric flow of test gas, second constant flow means for supplying a constant known volumetric flow of oxygen containing gas having a known oxygen amount which amount is more than that needed to completely oxidize the test gas, means defining a catalytic burning chamber containing a catalyst and connected to said first and second flow means for receiving the test and oxygen containing gases and completely catalytically burning the test gas with oxygen in the oxygen containing gas to consume an amount of oxygen which is proportional to the calorific value of the test gas, heating means for heating the burning chamber for catalytic burning, an electrochemical oxygen measuring cell connected to said chamber for receiving products of the catalytic burning therefrom and measuring the amount of remaining oxygen in the product and circuit means connected to the cell for generating a value proportional to the difference between the known volumetric flow of oxygen and the remaining oxygen in the product which value is proportional to the amount of oxygen consumed and in turn proportional to the calorific value of the test gas.

Another object of the invention is to provide a method of continuously measuring the calorific value of a test gas comprising providing test gas and oxygen containing gas at constant flow rates to a catalytic burning chamber, catalytically burning the test gas with oxygen in the chamber and measuring the remaining oxygen content of the combustion products whereby the amount of oxygen consumed can be determined which is proportional to the calorific value of the test gas.

A still further object of the invention is to provide a calorimeter which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawing and descriptive matter in which a preferred embodiment of the invention is illustrated.

BRIEF DESCRIPTION OF THE DRAWINGS

In the Drawings:

FIG. 2 is a schematic representation of an apparatus according to the invention.

DETAILED DESCRIPTION OF THE PREFERRED EMBODIMENT

Figure 1:
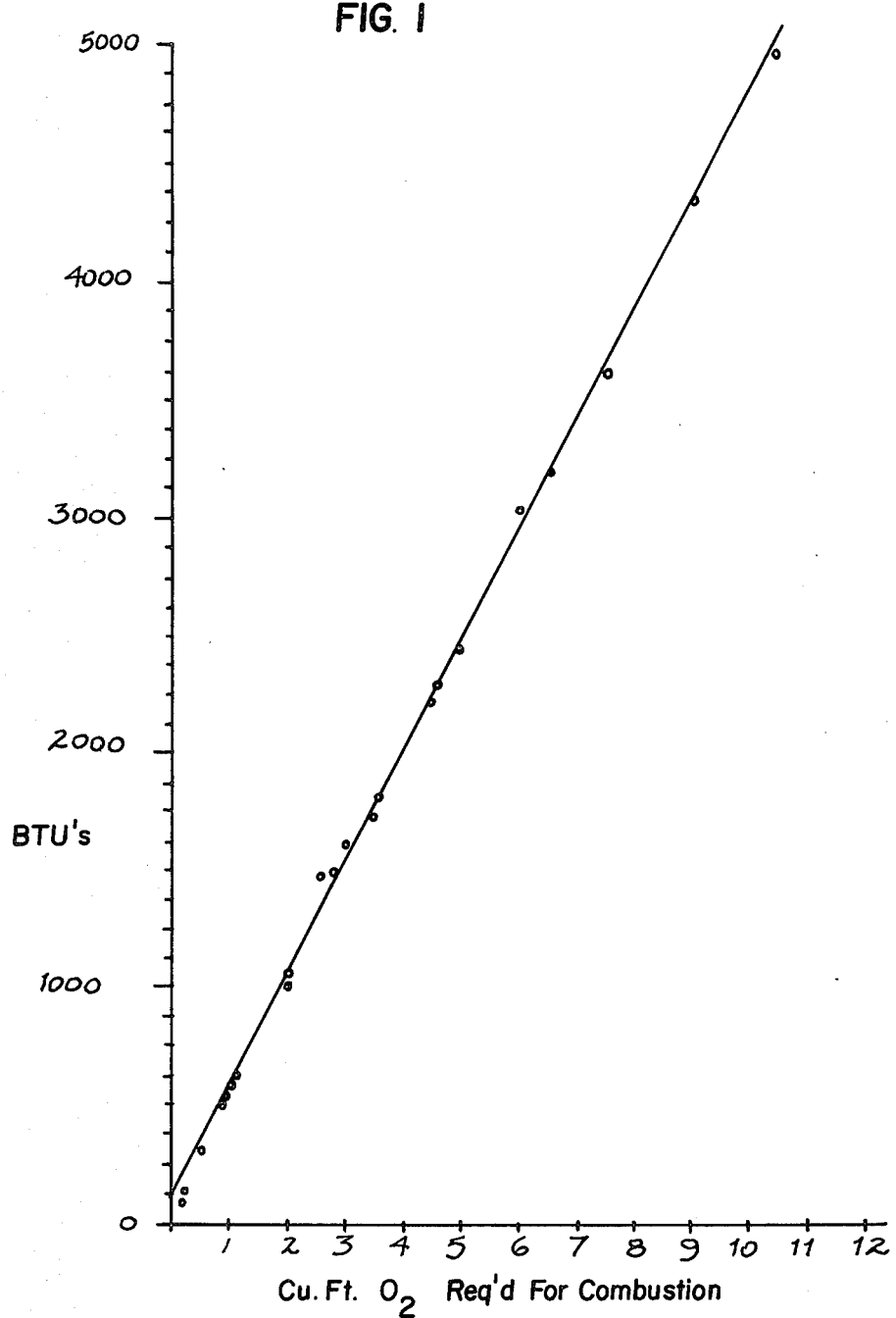
FIG. 1 is a graph showing the relationship between calorific value in BTU's versus cubic feet of oxygen required for combustion.

Referring to the drawings in particular, the invention embodied therein in FIG. 2 comprises a calorimeter generally designated 50 which utilizes a measuring cell 60 to measure the amount of remaining oxygen in a mixture of combustion products in a catalytic burning chamber 10 defined in a heated block 12. Heated block 12 is heated by a heating element schematically represented at 14.

Oxygen containing gas, preferably air, is provided over an inlet line 16 to a constant flow pump 18. Constant flow pump 18 may be of any type which can be accurately regulated for supplying a constant volumetric flow rate, such as a reciprocating cylinder pump having appropriate switching valves. The operation of constant flow pump 18 can also be regulated to insure constant pressure so that no compensation is necessary for changes in specific gravity of the air. The sample or test gas which may for example be a fuel or other oxidizable gas, is provided over a test gas inlet line 20 to another constant flow pump 22. The volumetric flow rate of the sample gas as well as the air is thus known. The two gases are mixed and provided to the catalytic burning chamber 10 which is serpentine for a complete combustion of the combustible elements in the test sample. Heating means 14 is operable to maintain the heat of the heated block 12 at a temperature of about 1500° F. From catalytic combustion or burning chamber 10 the products with now reduced oxygen is supplied over line 24. The flow then is divided between a bypass line going to the measuring cell 60 and a line 26. After cell 60 the gas is reunited and provided over line 28 to an outlet. Inspection plugs 30, 32 may be provided for inspecting various lines in the system and a test gas port 34 may also be provided for tapping a sample of combustion product.

The measuring cell 60 is preferably a known electrochemical $ZrO_2$ fuel cell for example of the type disclosed in the above-identified Hickam et al patent.

A signal generated by measuring cell 60 is processed by a circuit represented at 36. Circuit 36 analyzes the signal from measuring cell 60 and is operable to determine the amount of oxygen remaining in the combustion mixture. Since the amount of oxygen initially supplied by constant flow pump 18 is known as well as the amount of test sample or fuel supplied by constant flow pump 22, the amount of oxygen actually consumed in the catalytic combustion chamber 10 can be calculated, which oxygen amount is proportional to the calorific value of the test gas.

FIG. 1 demonstrates the linear relationship between calorific value in BTU's and amount of oxygen utilized in the combustion of various combustible gases or fuels. As shown in the Table, the calorific value of various combustible gases is directly proportional to the amount of oxygen needed to completely burn the same amount of the test gas. These values and other relevant information can be obtained from Handbook of Chemistry, N. A. Lange, Handbook Publishers, Inc., Sandusky, Ohio, 1952, pages 802–803.

It is noted that according to the invention more than enough air must be provided by pump 18 to completely burn all oxidizable components of the sample gas supplied by pump 22. This insures the maintenance of residual oxygen in the combustion products.

Since the amount of required oxygen is not necessarily dependent on the hydrogen-carbon ratio of the fuel or test gas, the inventive arrangement is usable for a wide variety of fuels for example as set forth in the Table.

TABLE

COMBUSTION CONSTANTS OF GASES

| Name | BTU/Cu. Ft., gross 60° F., 30 in. Hg, satd.$H_2O$ | Cu. Ft. $O_2$ Req'd. per cu. ft. of gas |
|---|---|---|
| Acetylene | 1456 | 2.5 |
| Benzene | 3658 | 7.5 |
| Butane | 3204 | 6.5 |
| Butylene | 3033 | 6.0 |
| Carbon Monoxide | 317.1 | 0.5 |
| Ethane | 1731 | 3.5 |
| Ethylene | 1613 | 3.0 |
| Hydrogen | 318.8 | 0.5 |
| Methane | 995 | 2.0 |
| Propane | 2465 | 5.0 |
| Propylene | 2313 | 4.5 |
| Toluene | 4364 | 9.0 |
| Xylene | 5064 | 10.5 |
| Blast Furnace Gas | 93 | .14 |
| Blue Water Gas | 310 | .456 |
| Carburetted Water Gas | 578 | .970 |
| Coal Gas | 634 | 1.100 |
| Coke Oven Gas (1) | 536 | .930 |
| Coke Oven Gas (2) | 600 | 1.056 |
| Natural Gas (Follansbee, W. Va.) | 2220 | 4.300 |
| Natural Gas Residual (Follansbee, W. Va.) | 1868 | 3.594 |
| Natural Gas (McKean Co., Pa.) | 1482 | 2.850 |
| Natural Gas (Sandusky, Ohio) | 1047 | 2.008 |
| Oil Gas | 516 | .850 |
| Producer Gas | 136 | .216 |

Catalytic burning is preferred over flame burning due to the possibility of completely burning all combustible products in the test sample. To overcome a possible problem in catalyst poisoning, a relatively large catalytic bed is utilized in chamber 10 to prolong catalyst life.

According to the invention rapid calorific values can be obtained without time delay which is normal in prior art calorimeters.

What is claimed is:

1. A calorimeter for the continuous monitoring of the calorific value of a test gas comprising:

first constant flow means for supplying a constant known volume of test gas;

second constant flow means for supplying a constant known volume of oxygen containing gas having a known oxygen amount which is more than that needed to completely oxidize the test gas;

means defining a catalytic burning chamber connected to said first and second flow means for receiving the test and oxygen containing gases and completely catalytically burning the test gas with an amount of oxygen of the oxygen containing to produce a combustion product having residual oxygen therein;

heating means for heating the catalytic burning chamber to produce catalytic burning;

an electrochemical oxygen measuring cell connected to said chamber for receiving the combustion product and measuring the remaining oxygen in the product; and circuit means connected to said cell for generating a value proportional to the difference between the known volume of oxygen and the amount of remaining oxygen which value is proportional to the amount of oxygen consumed in the combustion chamber, the amount of oxygen consumed being proportional to the calorific value of the test gas.

2. A calorimeter according to claim 1, wherein said first and second flow means comprise first and second constant flow pumps.

3. A calorimeter according to claim 2, wherein said first and second pumps comprise reciprocating cylinder pumps.

4. A calorimeter according to claim 1, wherein said electrochemical oxygen measuring cell comprises a $ZrO_2$ fuel cell.

5. A method of continuously monitoring the calorific value of a gas comprising:
supplying the test gas at a constant known flow rate to a catalytic combustion chamber;
supplying an oxygen containing gas to the catalytic burning chamber at a known constant flow rate;
heating the catalytic burning chamber to completely burn the test gas to consume an amount of oxygen and produce a combustion product with remaining oxygen therein;
measuring the amount of remaining oxygen in a combustion product; and
determining the catalytic value of the test gas which is proportional to the amount of oxygen consumed in the catalytic burning chamber which amount of oxygen consumed is proportional to the difference between the known volumetric flow of oxygen into the chamber and the amount of residual oxygen in the combustion product.

* * * * *